(12) United States Patent
Zhang et al.

(10) Patent No.: US 10,898,509 B2
(45) Date of Patent: Jan. 26, 2021

(54) OXIDIZED α-1,4-OLIGOGLUCURONIC ACID, AND PREPARATION METHOD THEREFOR AND USES THEREOF

(71) Applicant: SHANGHAI GREEN VALLEY PHARMACEUTICAL CO., LTD., Shanghai (CN)

(72) Inventors: Zhenqing Zhang, Suzhou (CN); Jie Hao, Suzhou (CN); Shichang Sun, Suzhou (CN); Huiling Zhang, Suzhou (CN)

(73) Assignee: SHANGHAI GREEN VALLEY PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/576,477

(22) PCT Filed: May 20, 2016

(86) PCT No.: PCT/CN2016/082929
§ 371 (c)(1),
(2) Date: Nov. 22, 2017

(87) PCT Pub. No.: WO2016/188382
PCT Pub. Date: Dec. 1, 2016

(65) Prior Publication Data
US 2018/0207195 A1 Jul. 26, 2018

(30) Foreign Application Priority Data
May 22, 2015 (CN) .......................... 2015 1 0267211

(51) Int. Cl.
*A61K 31/715* (2006.01)
*A61P 25/00* (2006.01)
*A61P 9/10* (2006.01)
*C07H 7/033* (2006.01)
*C08B 31/18* (2006.01)
*C07H 1/00* (2006.01)
*C07H 15/04* (2006.01)
*C08L 3/10* (2006.01)
*C07C 31/08* (2006.01)
*C07C 31/04* (2006.01)

(52) U.S. Cl.
CPC .............. *A61K 31/715* (2013.01); *A61P 9/10* (2018.01); *A61P 25/00* (2018.01); *C07H 1/00* (2013.01); *C07H 7/033* (2013.01); *C07H 15/04* (2013.01); *C08B 31/18* (2013.01); *C08L 3/10* (2013.01); *C07C 31/04* (2013.01); *C07C 31/08* (2013.01)

(58) Field of Classification Search
CPC ....... A61K 31/715; C07H 7/033; A61P 25/00; A61P 9/10; C07C 31/04
USPC ......................................................... 514/54
See application file for complete search history.

(56) References Cited

U.S. PATENT DOCUMENTS

| 5,831,043 A | * | 11/1998 | Fleche | .................... C07C 51/29 |
| | | | | 536/18.5 |
| 5,981,742 A | * | 11/1999 | Fleche | .................... C07H 15/04 |
| | | | | 536/123.1 |
| 2003/0119761 A1 | | 6/2003 | Christian | |
| 2010/0143513 A1 | | 6/2010 | Lee et al. | |

FOREIGN PATENT DOCUMENTS

CN       104892792 A     9/2015
WO    2014/200880 A1    12/2014

OTHER PUBLICATIONS

Glossary of medical education terms, Institute of International Medical Education. http://www.iime.org/glossary.htm Accessed in Mar. 2013. (Year: 2013).*
Liu et al. A review of bioactive plant polysaccharides: Biological activities, functionalization, and biomedical applications. Bioactive Carbohydrates and Dietary Fibre 5:31-61, 2015. (Year: 2015).*
Walaszek et al. D-Glucaric Acid Content of Various Fruits and Vegetables and Cholesterol-Lowering Effects of Dietary D-Glucarate in the Rat. Nutrition Research, vol. 16, No. 4. pp. 673-481, 1996. (Year: 1996).*
Sun et al., "Synthesis of a-D-glucuronic acid by catalytic oxidation with TEMPO/NaBr/NaClO system," Chemical Research and Application, Dec. 2012, vol. 24, No. 12, pp. 1777-1780.
Aug. 23, 2016 International Search Report issued in International Patent Application No. PCT/CN2016/082929.
Jan. 10, 2019 Supplementary European Search Report issued in European Patent Application No. 16 79 9270.
Thaburet, J. F., et al., "TEMPO-mediated oxidation of maltodextrins and D-glucose: effect of pH on the selectivity and sequestering ability of the resulting polycarboxylates", Carbohydrate Research, vol. 330, No. 1, pp. 21-29, 2001.
Pressey, Russell, "Oxidized Oligogalacturonides Activate the Oxidation of Indoleacetic Acid by Peroxidase", Plant Physiology, vol. 96, No. 4, pp. 1167-1170, 1991.
Schämann, M., et al., "Reaction of enamines and mediated anodic oxidation of carbohydrates with the 2,2,6,6-tetramethylpiperidine-1-oxoammonium ion (TEMPO+)", Electrochimica Acta, vol. 50, No. 25-26, pp. 4956-4972, 2005.

(Continued)

*Primary Examiner* — Yih-Horng Shiao
(74) *Attorney, Agent, or Firm* — Oliff PLC

(57) ABSTRACT

An oxidized α-1,4-oligoglucuronic acid, and a preparation method therefor and uses thereof. By using abundant starch, especially soluble starch, in the natural world as the raw material, all 6-site hydroxyl groups of the starch α-1,4-polyglucose are oxidized into carboxyl groups to form glucuronic acid under the action of a sodium bromide (NaBr)-2,2,6,6-tetramethyl piperidine oxide (TEMPO)-sodium hypochlorite (NaClO) oxidation system, and the oxidized oligoglucuronic acid having an open ring at an end is prepared by controlling reaction conditions. The compound has obvious anti-cerebral ischemia activity, and can be developed into a potential anti-cerebral ischemia drug.

18 Claims, 13 Drawing Sheets

(56) References Cited

OTHER PUBLICATIONS

Oct. 12, 2019 Chinese Search Report issued in Chinese Patent Application No. 201680029752.8.
Kato, Y., "Oxidation process of water-soluble starch in TEMPO-mediated system", Elsevier Carbohydrate Polymers 51, (2003), pp. 69-75.

* cited by examiner

OXIDIZED α-1,4-OLIGOGLUCURONIC ACID, AND PREPARATION METHOD THEREFOR AND USES THEREOF

TECHNICAL FIELD

The present invention belongs to the technical field of pharmaceutical compounds, and in particular, relates to an oxidized α-1,4-oligoglucuronic acid and preparation methods as well as uses thereof.

BACKGROUND

Starch is mainly present in leaves, roots and seeds of plants in a granular form. Starch is composed of linear amylose and amylopectin. Amylase is connected in α1→4 mode, which can be soluble in hot water to obtain a clear solution. Amylopectin is also a α1→4 glucan, however, it also contains α1→6 branches in structure, which can not be soluble in cold water, and become viscous in hot water.

Soluble starch is a starch derivative obtained by treating starch with oxidants, acids, glycerol, enzymes or through other methods. Soluble starch is a white or light yellow powder, tasteless and odorless. Soluble starch is a denatured starch, soluble in hot water, and insoluble in cold water, alcohol and ether. Generally, starch of rice, corn, millet, potato can be used to prepare into soluble starch, but the soluble starch prepared from the starch of sweet potato is of the best quality. Soluble starch can be edible, and also can be industrially used in the preparation of dextrin, maltose, glucose, alcohol, and the like, and can be used in industries, such as printing, textile, pharmaceutical and the like.

Glucuronic acid is a common carbohydrate molecule which, in body acts as part of the composition of glycosaminoglycan, such as heparan sulfate, chondroitin sulfate, and the like; and also appears in glycosyl moiety of small molecule glycosides. However, there is no poly-glucuronic acid or oligo-glucuronic acid in nature.

In recent years, the incidence and mortality of cerebrovascular diseases increase with the improvement of living standards and the aging of population, which have become one of the leading causes of death. Among them, ischemic cerebrovascular disease is a major part of cerebrovascular diseases. At present, drugs that have good therapeutic effects on cerebral ischemic diseases include traditional Chinese medicine compositions, traditional Chinese medicines, and the like, however the clinical efficacy of these drugs remains to be confirmed yet. Therefore, it is of great significance to study new anti-cerebral ischemia drugs.

SUMMARY OF THE INVENTION

In view of the defects in the prior art, an oxidized α-1,4-oligoglucuronic acid and preparation methods as well as uses thereof are provided. In the method of the invention, starch abundant in nature, especially soluble starch is used as raw materials, all of 6-position hydroxyl of starch, α-1,4-polyglucose are oxidated to carboxyl to form glucuronic acid by the action of sodium bromide (NaBr)-2,2,6,6-tetramethylpiperidine oxide (TEMPO)-hypochlorite (NaClO) oxidation system, and at the same time, oxidized oligoglucuronic acid with end-opened ring is prepared by controlling the reaction conditions. This type of compounds exhibits significant anti-cerebral ischemia activity and can be developed into potential anti-cerebral ischemia drugs.

The object of the present invention is achieved by following technical solutions:

In one aspect of the present invention, an oxidized α-1,4-oligoglucuronic acid with structure of general formula I and degree of polymerization of 1 to 20 is provided:

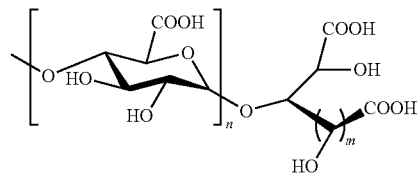

Formula I wherein n=0-19; and m=0, 1 or 2.

In another aspect of the present invention, a mixture of the above-mentioned oxidized α-1,4-oligoglucuronic acids consisting of oxidized α-1,4-oligoglucuronic acids having structure of general formula I' is provided

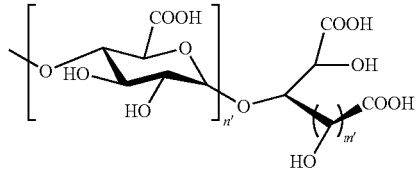

Formula I' wherein n' and m' are average values of n and m for each oligo-glucuronic acid in the mixture, respectively, n' is selected from 1.0 to 19.0; and m' is selected from 0 to 2.0. n' and m' can be integers or non-integers, which are arithmetic means of n and m for each oligo-glucuronic acid in the mixture on a molar basis.

A further aspect of the invention relates to a process for preparing oxidized α-1,4-oligoglucuronic acid or mixtures thereof, comprising steps of:

(1) weighing soluble starch and preparing it into aqueous solution;

(2) sequentially adding TEMPO and sodium bromide to the aqueous solution prepared in step (1), adjusting pH to 10-11 with an alkaline pH adjuster, then adding a sodium hypochlorite solution and reacting for 5-10 hours at 40-70° C., and finally adding an organic solvent to quench the reaction;

(3) obtaining a mixture of oxidized α-1,4-oligoglucuronic acids through dialysis in a 500 Da dialysis bag, concentration and lyophilization, or optionally obtaining individual oxidized α-1,4-oligoglucuronic acid through chromatographic separation.

The present invention also relates to a composition, comprising the oxidized α-1,4-oligoglucuronic acids of general formula I according to the present invention or a mixture thereof and a pharmaceutically acceptable excipient or carrier.

In another aspect of the present invention, the use of the oxidized α-1,4-oligoglucuronic acid according to the present invention or a mixture thereof in the preparation of anti-cerebral ischemia drugs or brain nerve-protecting drugs is also provided. They can be used to treat or prevent ischemic damage to neurons caused by stroke, myocardial infarction, brain shock, neonatal asphyxia and traumatic brain injury.

In another aspect of the invention, a method is also provided for treating or preventing neuronal ischemic damage in a subject or protecting brain nerves of a subject, comprising administering to the subject an effective amount of the oxidized α-1,4-oligoglucuronic acid of general formula I or a mixture thereof.

In the present invention, oxidized α-1,4-oligoglucuronic acids of general formula I or a mixture thereof as an agent for treating or preventing neuronal ischemic damage or as an agent for protecting brain nerves is also provided.

In the above solutions, the neuronal ischemic damage is caused by stroke, myocardial infarction, brain shock, neonatal asphyxia and traumatic brain injury.

Outstanding effects of the present invention include: soluble starch is used as a raw material for preparing oxidized α-1,4-oligoglucuronic acid, the preparation method is simple, conditions are mild, the cost is low, and it is readily to be industrialized. At the same time, these compounds possess significant anti-ischemic activities, and can be used to treat ischemic damage caused by stroke, myocardial infarction, brain shock, neonatal asphyxia and traumatic brain injury.

For readily understanding and grasping the technical solutions of the present invention, specific embodiments of the present invention will be further described below with reference to the accompanying drawings of the embodiments.

MODE FOR CARRYING OUT THE INVENTION

Figure 1:
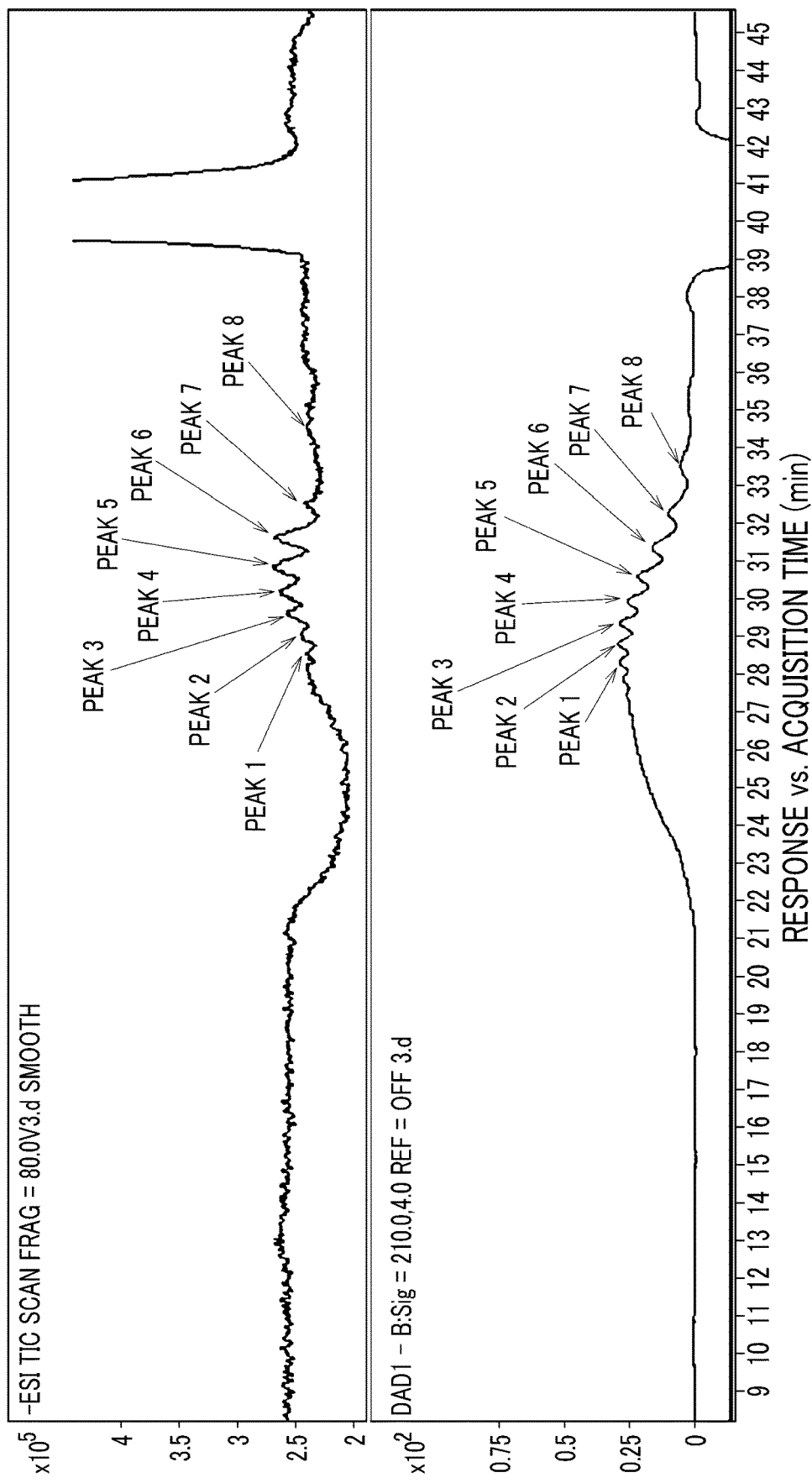
FIG. 1 is a total ion chromatography (TIC) and a UV chromatogram at 210 nm of oxidized α-1,4-oligoglucuronic acid of Example 5.

The method of the present invention will be described below by way of specific examples, but the present invention is not limited thereto.

The first aspect of the present invention relates to an oxidized α-1,4-oligoglucuronic acid of the following general structure I:

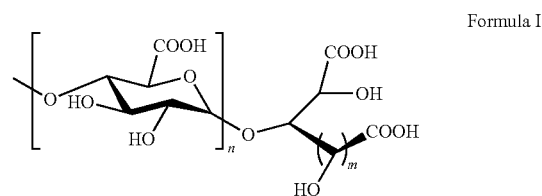

Formula I wherein n=0-19; m=0, 1 or 2.

When m=0, the terminal glucose molecule is oxidized to remove two —CH(OH)— units, when m=1, the terminal glucose molecule is oxidized to remove one —CH(OH)— unit, and when m=2, —CH(OH)— is not removed from the terminal glucose molecule, and only oxidation of hydroxyl occurs. In an oxidized α-1,4-oligoglucuronic acid, i.e., oxidized α-1,4-oligoglucuronic acid in which n is a certain number, products wherein m is 0, 1, and 2 can be present in a mixture, or can be individually present. Oxidized α-1,4-oligoglucuronic acids with different m values will possess similar biological activities.

In a preferred embodiment of the present invention, n is 1 to 9, which corresponds to disaccharide to decaccharide of the oxidized α-1,4-oligoglucuronic acid, each of which is separated and characterized in the present invention. More specifically, in the oxidized α-1,4-oligoglucuronic acid of formula I, when n is 1, it corresponds to oxidized disaccharide; when n is 2, it corresponds to oxidized trisaccharide, when n is 3, it corresponds to oxidized tetrasaccharide, when n is 4, it corresponds to oxidized pentasaccharide, when n is 5, it corresponds to oxidized hexasaccharide, when n is 6, it corresponds to oxidized heptasaccharide, when n is 7, it corresponds to oxidized oct-saccharide, when n is 8, it corresponds to oxidized nonus-saccharide, and when n is 9, it corresponds to oxidized decasaccharide. These oxidized oligosaccharides may be used in a form of one or more mixtures.

The oxidized α-1,4-oligoglucuronic acid of the present invention is characterized by an oligo-uronic acid structure of different carbon atoms with end-opened ring. In one embodiment, oligo-glucuronic acids of different forms at reducing ends may be present as a mixture and the oligo-glucuronic acid of different polymerization degrees may also be present as a mixture.

Another aspect of the invention relates to a mixture of oxidized α-1,4-oligoglucuronic acids with a structure of general formula I'

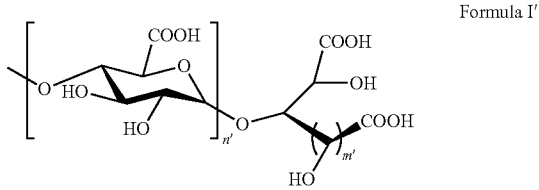

Formula I' wherein n' and m' are average values of n and m for each oligoglucuronic acid in a mixture, respectively, n' is selected from 1.0 to 19.0; m' is selected from 0 to 2.0. More preferably, n' is selected from 1.0 to 10.0 and m' is selected from 0.5 to 1.8; and most preferably n' is selected from 1.0 to 9.0 and m' is selected from 0.8 to 1.5.

In another preferred embodiment, the oxidized α-1,4-oligoglucuronic acid mixture of the invention comprises more than 80%, preferably more than 90%, more preferably more than 95% of dimer to decamer of α-1,4-glucuronic acid (n is 1-9) with end-opened ring, where m' is 0.8-1.5.

The oxidation process of the present invention comprises steps of dissolving starch, oxidizing the starch solution, and post-treating oxidized products to form oxidized α-1,4-oligoglucuronic acid.

1. Dissolution of Starch

To prepare the oxidized α-1,4-oligoglucuronic acid of the present invention, the raw material, soluble starch is dissolved in water to form an aqueous solution. The concentration of the starch solution may be about 1 to 30 mg/mL. In particular, the amount of water is 50-100 ml per gram of soluble starch. The applicant found that if the concentration of starch solution is too high, it is not easy to completely perform the oxidation process, and if the concentration of starch solution is too low, it will result in unhomogeneous products.

2. Oxidation of Starch Solution

The following oxidation system was used in the present invention: sodium bromide (NaBr)-2,2,6,6-tetramethylpiperidine oxide (TEMPO)-sodium hypochlorite (NaClO) oxidation system. Oxidation performance of the oxidation system is particularly suitable for obtaining the α-1,4-oligoglucuronic acid of the present invention by adjusting reaction conditions. Compared with conventional oxidants, the oxidation system of the present invention enables the oxidation reaction to proceed more completely so as to obtain a reaction product with end-opened ring without impairing the uniformity of the reaction system. In addition, proportions of substances in the oxidation system on a molar basis may be, for example, TEMPO:NaBr=1:5 to 1:50; glucose units in starch:active NaClO=1:0.5 to 1:5; TEMPO: Glucose unit in starch=1:1 to 1:5. In one embodiment of the present invention, the weight percentage of active sodium hypochlorite in the sodium hypochlorite solution is 1 to 20%, preferably 2 to 15%, more preferably 3 to 12%.

The oxidation reaction is carried out under alkaline conditions. Upon research, it was found that the optimum pH range is 10-11. When the pH value of the reaction system is too high, the oxidation efficiency is low. If the pH value is too low, it is not conducive to the oxidation. The pH value of the reaction is controlled by a basic compound, and the most preferred basic compound is NaOH solution. There is no particular restriction on NaOH solution.

The oxidation temperature of an oxidation reaction suitably used in the present invention is 40 to 70° C., preferably 45 to 60° C., more preferably 48 to 55° C. Oxidation within this temperature range will facilitate the removal of residual enzyme undesired in starch, while obtaining uronic acid with end-opened ring. Without being bound to any theory, the inventors have found that a reaction temperature below 40° C. will be unfavourable for obtaining oxidized α-1,4-oligoglucuronic acid with end-opened ring. And if the reaction temperature is too high, biological activities of raw starch materials will be destroyed, thereby unfavourable for using reaction products.

After adding an organic solution to quench the reaction, the product solution obtained by oxidation is purified to obtain oxidized α-1,4-oligoglucuronic acid. As a preferred purification method, the obtained oligoglucuronic acid can be purified by dialysis, and in particular, the material used for dialysis should entrap a substance with a molecular weight of 500 Da, thereby purifying the oligosaccharide of the present invention. Other purification methods known in the art can also be used, as long as the purity of the oligoglucuronic acid obtained by dialysis can be ensured to be higher than 99%, more preferably higher than 99.5%.

The present invention also relates to the use of oxidized α-1,4-oligoglucuronic acid or a mixture thereof as an active compound component for preparing anti-cerebral ischemia drugs. Cerebrovascular disease is the leading cause of death among middle-aged and elderly people in our country, and is also one of the focuses of the study of world health strategy. Among cerebrovascular diseases, the incidence of ischemic diseases ranks the first. In the case of mild ischemia/hypoxia, generally the brain compensatory mechanism protects central nervous system from injury. However, when the degree of ischemia is increased, irreversible nerve damages will occur, leading to a series of clinical symptoms and even death. Clinically, cerebrovascular accidents (such as stroke), myocardial infarction, shock, neonatal asphyxia and traumatic brain injury can cause ischemic damage to neurons. Therefore, it is of great significance to develop a natural source substance which can alleviate symptoms of cerebral ischemia and enhance the survival rate of brain cells.

The cell model used in the present invention for measuring symptoms of cerebral ischemia is a cell (OGD model) produced from HT-22 cells under oxygen and glucose deprivation conditions. HT-22 cells are a mouse hippocampal neuronal cell line that is a subclone of mouse T4 cell line and possesses characteristics of hippocampal neurons. Relevant contents can be found in, for example, Jeney Ramirez-Sanchez et al., Neurochemistry International 90 (2015) 215-223, "Neuroprotection by JM-20 against oxygen-glucose deprivation in rat hippocampal slices: Involvement of the Akt/GSK-Pathological"; Xiao-Jing Li et al., Journal of Ethnopharmacology 141 (2012) 927-933, Neuroprotective effects of Tong Luo Jiu Nao in neurons exposed to oxygen and glucose deprivation; TIAN-ZHI ZHAO et al., Neuroscience 328 126, "GPER1 Mediates Estrogen-Induced Neuroprotection Against Oxygen-Glucose Deprivation In The Primary Hippocampal Neurons"; and the like.

The present inventors found that the oxidized α-1,4-oligoglucuronic acid of general formula I or a mixture thereof can improve symptoms of cerebral ischemia and increase the survival rate of ischemic and hypoxia brain cells. Additionally, the oxidized α-1,4-oligoglucuronic acid of the present invention is derived from a natural product and is easily to be absorbed and utilized. The present invention provides a pharmaceutical combination, comprising at least two oxidized α-1,4-oligoglucuronic acids as said above, and optionally a pharmaceutically acceptable excipient.

Methods for preparing various pharmaceutical combinations containing various proportions of active ingredients are known or will be apparent to a skilled person based on the disclosure of the present invention, which are, for example described in Remington's Pharmaceutical Sciences, Martin, E. W., ed., Mack Publishing Company, 19th ed. (1995). A method for preparing a pharmaceutical composition includes incorporation of a suitable pharmaceutical excipient, carrier, diluent and the like.

Pharmaceutical formulations of the present invention are manufactured by known methods, including conventional methods of mixing, dissolving or lyophilizing.

The pharmaceutical composition of the present invention can be administered to a patient in a variety of routes suitable for the selected administration mode, for example, orally or parenterally (by intravenous, intramuscular, topical or subcutaneous routes).

Therefore, the pharmaceutical combination of the present invention in combination with a pharmaceutically acceptable carrier (such as an inert diluent or an edible carrier) may be administered systemically, eg, orally. They can be enclosed in hard or soft shell gelatin capsules and can be compressed into tablets. For oral therapeutic administration, the active compounds of the present invention may be combined with one or more excipients and used in a form of swallowable tablet, buccal tablet, troche, capsule, elixir, suspension, syrup, disc and the like. Such composition and preparation should contain at least 0.1% of active compound. The proportions of such composition and preparation can of course vary and may range from about 1% to about 99% by weight of a given unit dosage form. In the therapeutically useful composition, the amount of active compound is such that an effective dosage level can be achieved.

Tablets, troches, pills, capsules and the like may also contain: binders such as gum tragacanth, acacia, corn starch or gelatin; excipients such as dicalcium phosphate; disintegrants such as corn starch, potato starch, alginic acid and the like; a lubricant such as magnesium stearate; and a sweetening agent such as sucrose, fructose, lactose or aspartame; or a flavoring such as peppermint, oil of wintergreen, or cherry. When the unit dosage form is a capsule, it may contain, in addition to the above type of material, a liquid carrier such as vegetable oil or polyethylene glycol. A variety of other materials may be present as a coating, or a physical form altering the solid unit dosage form by otherwise modes. For example, tablets, pills or capsules can be coated with gelatin, wax, shellac or sugar and the like. A syrup or elixir may contain the active compound, sucrose or fructose as a sweetening agent, methyl paraben or propyl paraben as a preservative, a dye and a flavoring such as cherry flavor or orange flavor. Of course, any material used to prepare any unit dosage form should be pharmaceutically acceptable and nontoxic in the employed amount. In addition, the active compounds can be incorporated into sustained release formulations and sustained release devices.

The active compounds can also be administered intravenously or intraperitoneally by infusion or injection. An aqueous solution of the active compound or salt thereof, optionally with a miscible non-toxic surfactant, may be prepared. Dispersants in glycerol, liquid polyethylene glycols, triacetin and mixtures thereof and oils may also be prepared. Under ordinary conditions of storage and use, these preparations contain a preservative to prevent the growth of microorganisms.

Pharmaceutical dosage forms suitable for injection or infusion may include a sterile aqueous solution or dispersions or sterile powder, where active ingredients in an instant preparation are contained in a suitable sterile injectable or infusible solution or dispersion agent (optionally encapsulated in liposomes). In all cases, the final dosage form must be sterile, liquid and stable under the conditions of manufacture and storage. Liquid carriers can be solvents or liquid dispersion media including, for example, water, ethanol, polyols (eg, glycerol, propylene glycol, liquid polyethylene glycols, etc.), vegetable oils, nontoxic glycerides, and suitable mixtures thereof. Proper fluidity can be maintained, for example, by forming liposomes, by maintaining the required particle size in the case of dispersions, or by using surfactants. Prevention of microorganisms can be brought about by various antibacterial and antifungal agents such as parabens, chlorobutanol, phenol, sorbic acid, thimerosal and the like. In many cases, it is preferable to include isotonic agents, such as sugars, buffers, or sodium chloride. Prolonged absorption of injectable compositions can be produced by using absorption-delayed compositions (eg, aluminum monostearate and gelatin).

Sterile injectable solutions are prepared by combining a required amount of active compounds in a suitable solvent with a required amount of various other ingredients enumerated above, followed by filtered sterilization. In the case of sterile powders for preparing sterile injectable solutions, the preferred method of preparation is vacuum drying and freeze-drying technique, which will produce a powder of the active ingredient with any otherwise required components present in a previously sterile-filtered solution.

Useful solid carriers include comminuted solids (such as talc, clay, microcrystalline cellulose, silica, alumina, etc.). Useful liquid carriers include water, ethanol or ethylene glycol or a water-ethanol/ethylene glycol mixture, in which an effective amount of the pharmaceutical combination of the present invention may optionally be dissolved or dispersed with the help of non-toxic surfactants. Adjuvants (such as flavouring agent) and additional anti-microbial agents can be added to optimize properties for a given use.

Thickeners (such as synthetic polymers, fatty acids, fatty acid salts and esters, fatty alcohols, modified celluloses or modified inorganic materials) may also be used in combination with liquid carriers for forming paintable pastes, gels, ointments, soap, etc., which can be directly applied on the user's skin.

The required therapeutic or prophylactic amount for a compound or a mixture thereof depends not only on the compound itself, but also on the administration mode, the nature of a disease to be treated, and the age and condition of a patient, and ultimately depends on the decision from an attending physician or clinician.

The above formulation may be presented in a unit dosage form, which is a physically discrete unit containing a unit dosage and suitable for administering to humans and other mammalian bodies. The unit dosage form can be a capsule or tablet, or many capsules or tablets. Depending on involved particular treatments, the unit dose of active ingredient may be varied or adjusted from about 0.1 to about 1000 mg or more.

The experimental methods described in the following examples are conventional methods unless otherwise specified. The reagents and materials are commercially available unless otherwise specified.

Example 1. Method for Preparing Oxidized α-1,4-oligoglucuronic Acid (1) 1 g of soluble starch was weighed, and dissolved in 50 ml of water for preparing an aqueous solution;

(2) To the aqueous solution prepared in step (1), 5 mg of TEMPO and 50 mg of sodium bromide were sequentially added, pH was adjusted to 10 with 5% NaOH solution, and 5 ml of sodium hypochlorite solution was added at a concentration of 5% weight on a basis of active hypochloric acid. At 50° C., the reaction was performed for 5 hours, and absolute ethanol was added to quench the reaction;

(3) Oxidized α-1,4-oligoglucuronic acid was obtained through dialysis in a 500 Da dialysis bag, concentration and lyophilization.

Example 2. Method for Preparing Oxidized α-1,4-oligoglucuronic Acid (1) 1 g of soluble starch was weighed, and dissolved in 75 ml of water for preparing an aqueous solution;

(2) To the aqueous solution prepared in step (1), 30 mg of TEMPO and 350 mg of sodium bromide were sequentially added, pH was adjusted to 10 with 20% NaOH solution, and 10 ml of sodium hypochlorite solution was added at a concentration of 5% weight on a basis of active hypochloric acid. At 45° C., the reaction was performed for 8 hours, and absolute ethanol was added to quench the reaction;

(3) Oxidized α-1,4-oligoglucuronic acid was obtained through dialysis in a 500 Da dialysis bag, concentration and lyophilization.

Example 3. Method for Preparing Oxidized α-1,4-oligoglucuronic Acid (1) 1 g of soluble starch was weighed, and dissolved in 100 ml of water for preparing an aqueous solution;

(2) To the aqueous solution prepared in step (1), 50 mg of TEMPO and 500 mg of sodium bromide were sequentially added, pH was adjusted to 11 with 30% NaOH solution, and 15 ml of sodium hypochlorite solution was added at a concentration of 5% weight on a basis of active hypochloric acid. At 55° C., the reaction was performed for 10 hours, and methanol was added to quench the reaction;

(3) Oxidized α-1,4-oligoglucuronic acid was obtained through dialysis in a 500 Da dialysis bag, concentration and lyophilization.

Example 4. Method for Preparing Oxidized α-1,4-oligoglucuronic Acid (1) 1 g of soluble starch was weighed, and dissolved in 100 ml of water for preparing an aqueous solution;

(2) To the aqueous solution prepared in step (1), 50 mg of TEMPO and 600 mg of sodium bromide were sequentially added, pH was adjusted to 11 with 50% NaOH solution, and 15 ml of sodium hypochlorite solution was added at a concentration of 5% weight on a basis of active hypochloric acid. At 50° C., the reaction was performed for 10 hours, and methanol was added to quench the reaction;

(3) Oxidized α-1,4-oligoglucuronic acid was obtained through dialysis in a 500 Da dialysis bag, concentration and lyophilization.

Example 5. Mass Spectrometry Test of Oxidized α-1,4-oligoglucuronic Acid 5.1 Method 2 mg of oxidized α-1,4-oligoglucuronic acid obtained in Example 1 was weighed and dissolved in 1 ml of pure water. After filtration through a 0.22 μm microporous membrane, ultra-high performance liquid chromatography in series four Rod-time-of-flight mass spectrometry (UHPLC/Q-TOF-MS) analysis was performed.

In UHPLC/Q-TOF-MS analysis, Agilent 6540 UHD Accurate-Mass Q-TOF LC/MS (Agilent Technologies, USA) system was used. Chromatographic conditions are listed as follows: ACQUITY UPLC BEH125 size exclusion chromatography column (4.6×300 mm, Waters); detection wavelength: 210 nm; mobile phase: A 50 mM ammonium acetate aqueous solution, B methanol, ratio 80% of A; flow rate 0.1 ml/min. Mass spectrometry conditions are listed as follows: negative ion mode; scanning range: 100-3000; temperature of dry gas: 350° C.; flow rate of dry gas: 8 L/min; capillary voltage: 3500 V; Fragment voltage: 80V.

5.2 Results

Figure 2:
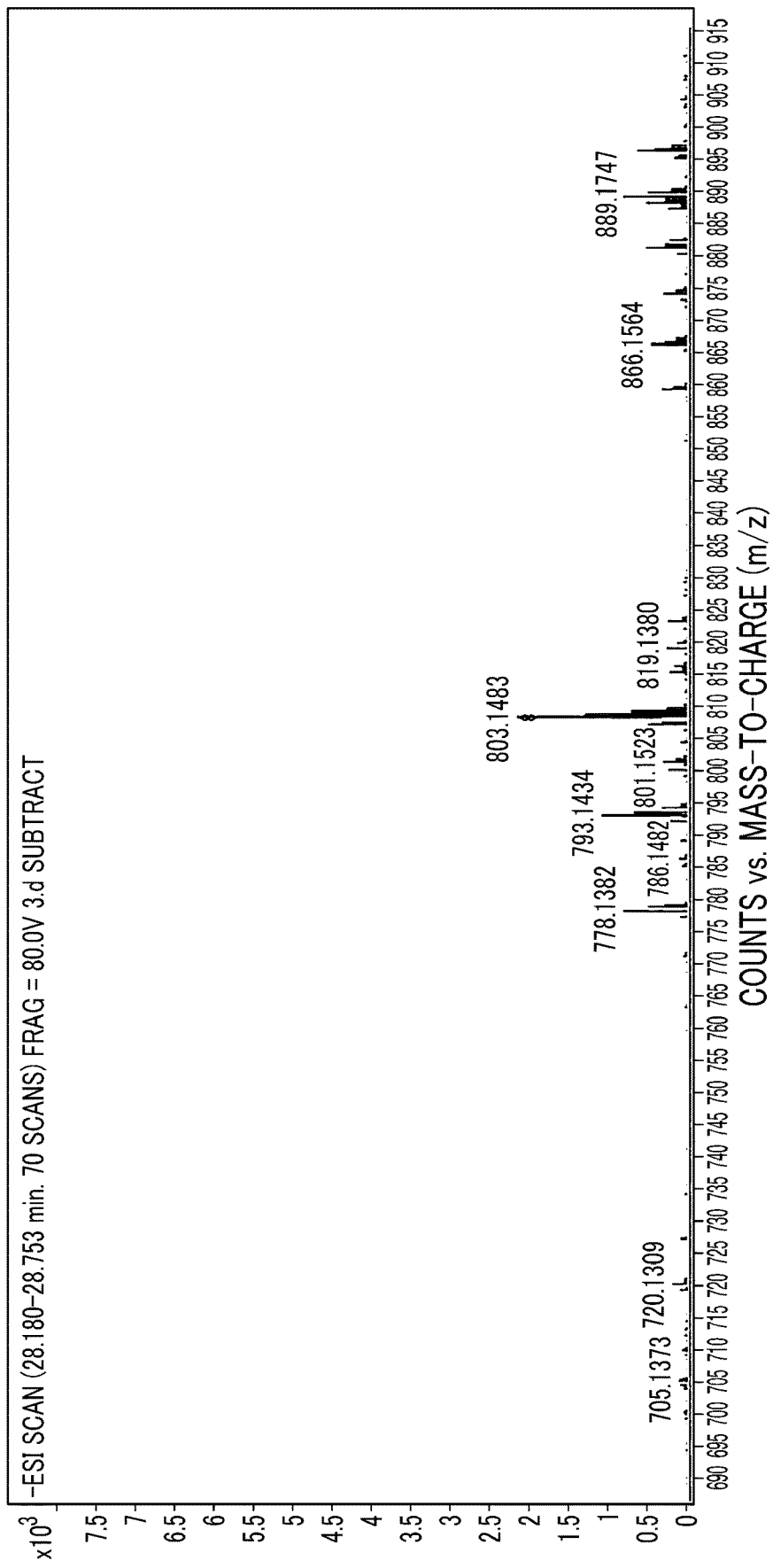
FIG. 2 is a mass spectrum of peak 1 in Example 5, i.e., a mass spectrum of oxidized α-1,4-oligoglucuronic acid nonus- and deca-saccharide.
Figure 3:
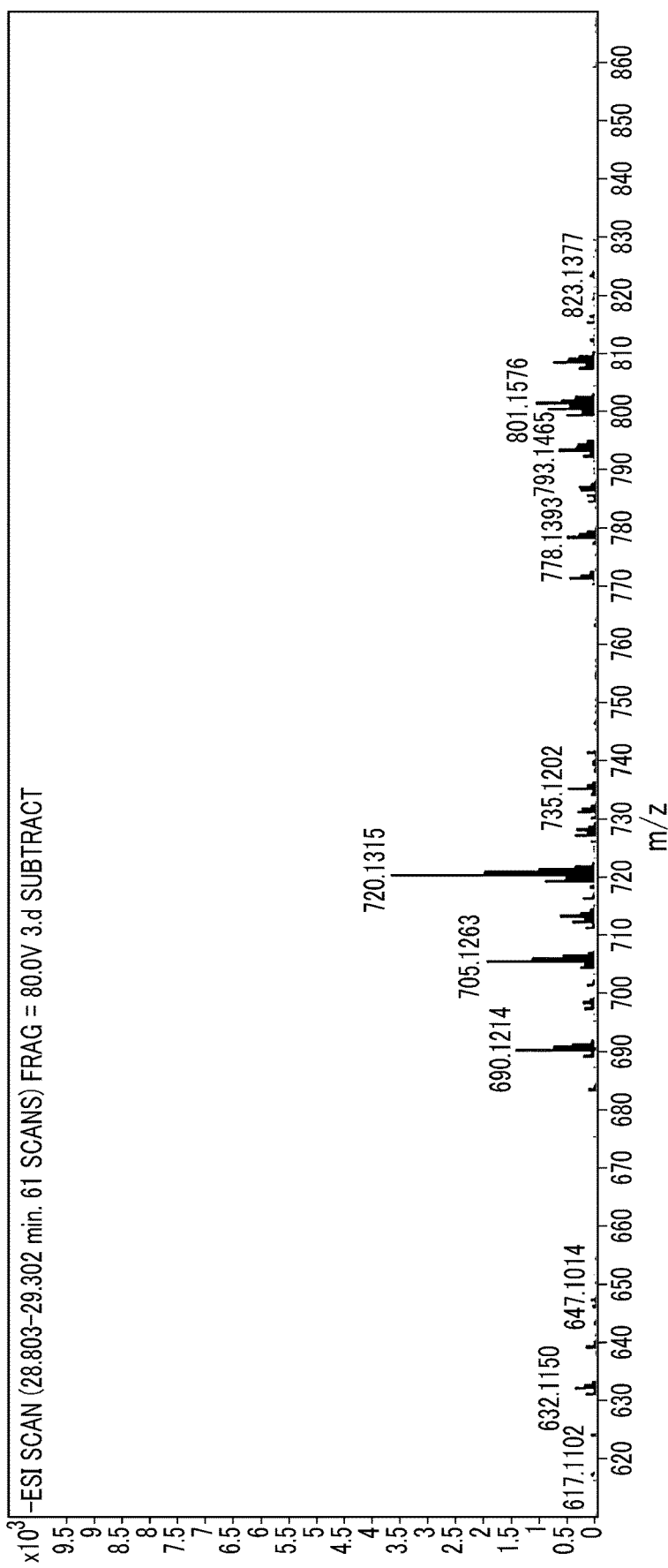
FIG. 3 is a mass spectrum of peak 2 in Example 5, i.e., a mass spectrum of oxidized α-1,4-oligoglucuronic acid oct-saccharide.
Figure 4:
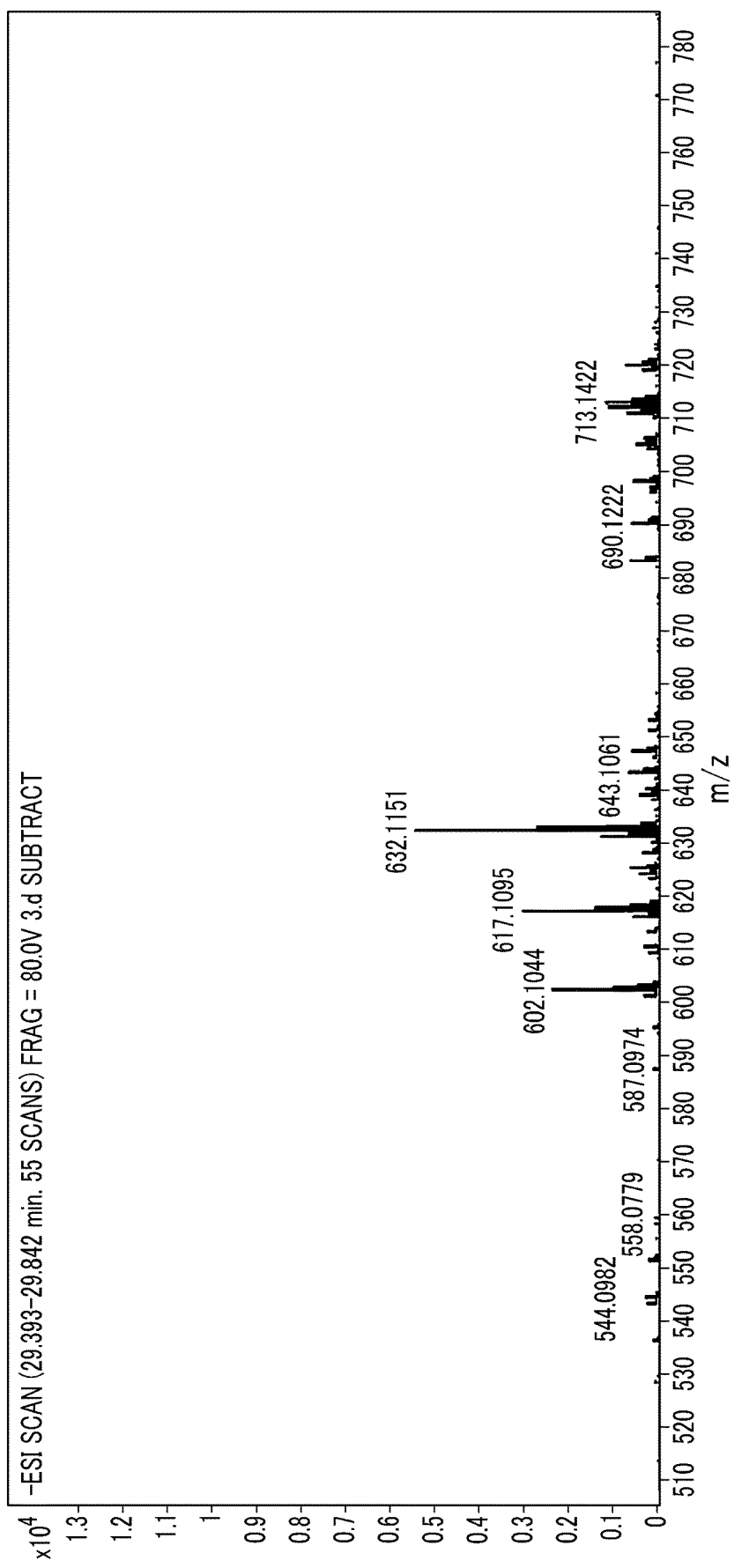
FIG. 4 is a mass spectrum of peak 3 in Example 5, i.e., a mass spectrum of oxidized α-1,4-oligoglucuronic acid hept-saccharide.
Figure 5:
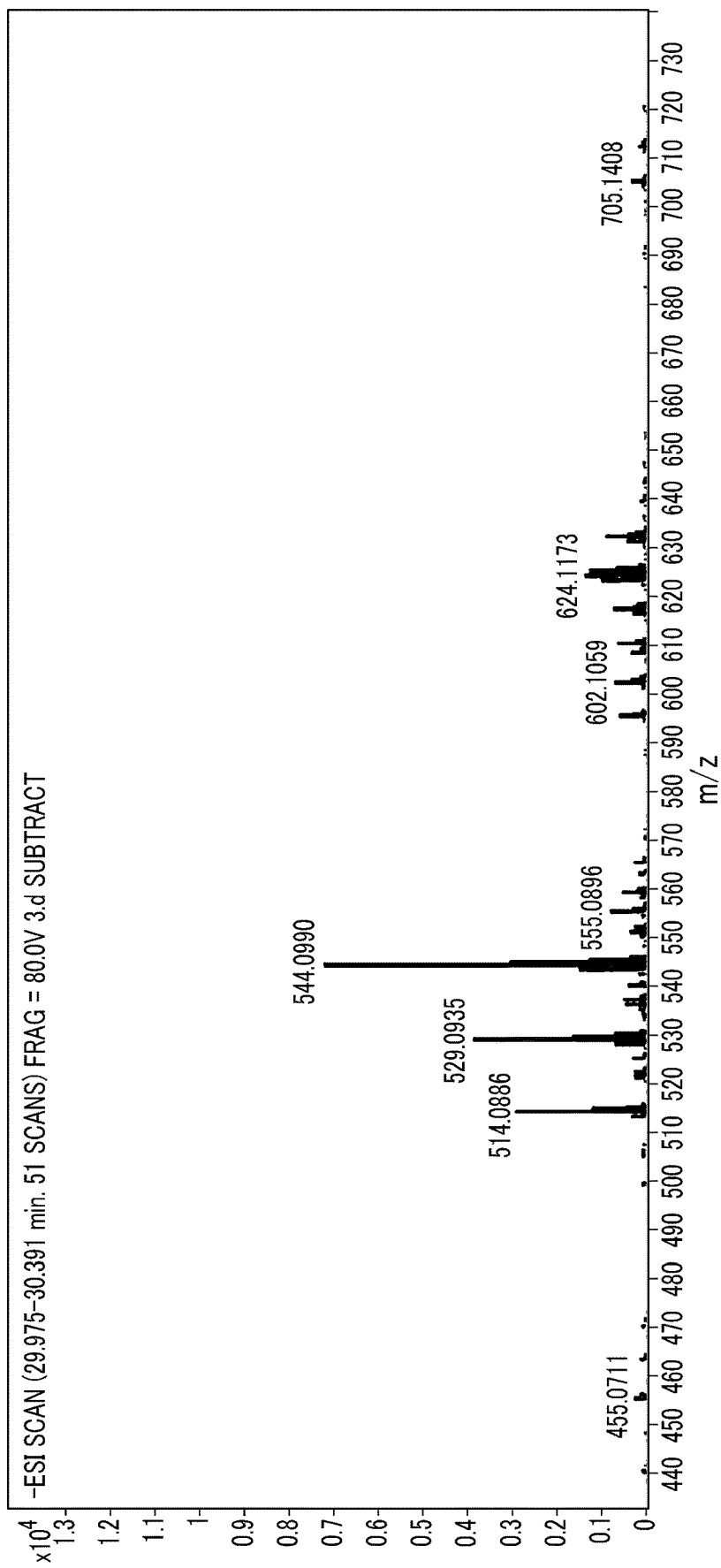
FIG. 5 is a mass spectrum of peak 4 in Example 5, i.e., a mass spectrum of oxidized α-1,4-oligoglucuronic acid hexa-saccharide.
Figure 6:
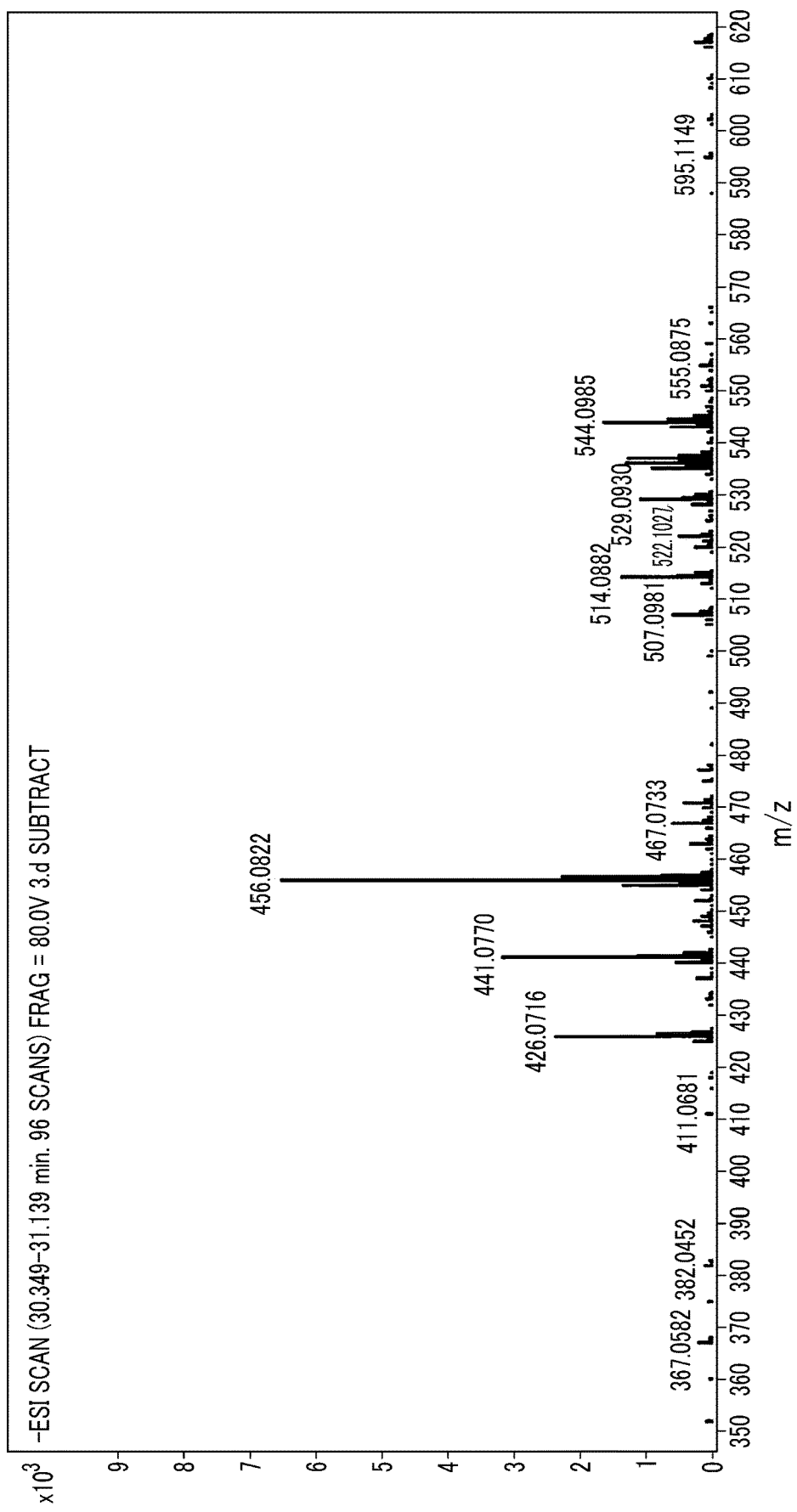
FIG. 6 is a mass spectrum of peak 5 in Example 5, i.e., a mass spectrum of oxidized α-1,4-oligoglucuronic acid penta-saccharide.
Figure 7:
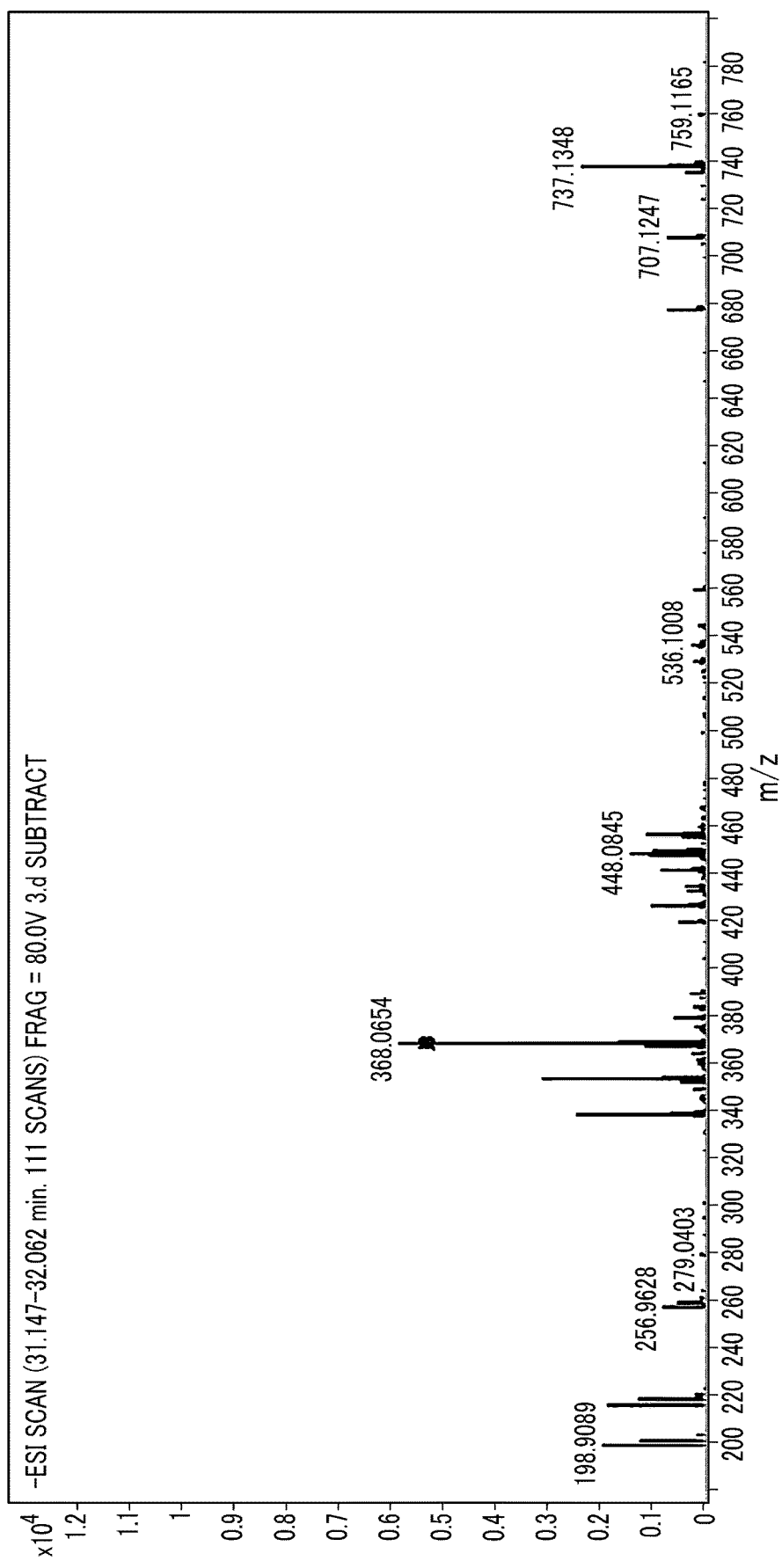
FIG. 7 is a mass spectrum of peak 6 in Example 5, i.e., a mass spectrum of oxidized α-1,4-oligoglucuronic acid tetra-saccharide.
Figure 8:
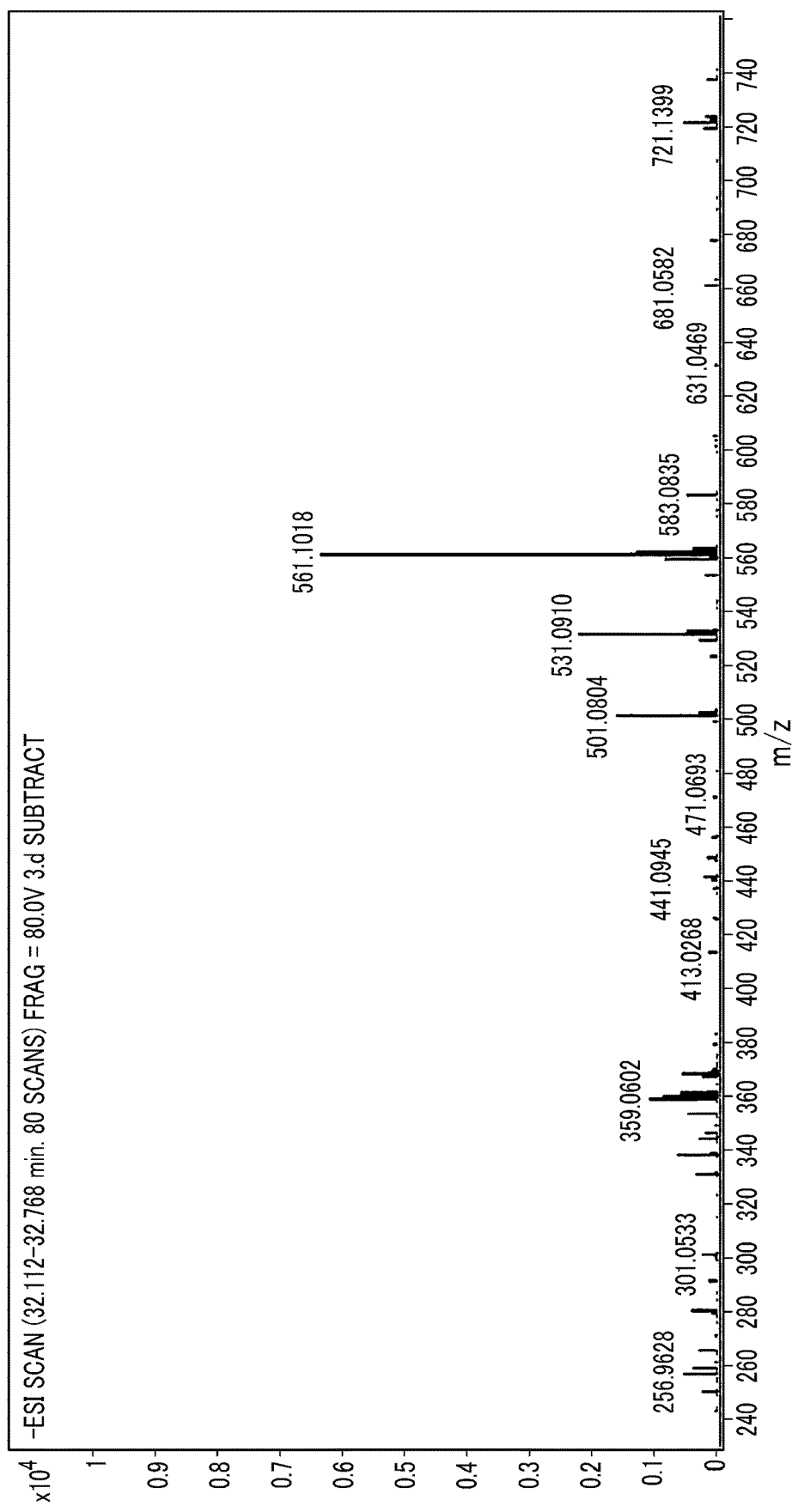
FIG. 8 is a mass spectrum of peak 7 in Example 5, i.e., a mass spectrum of oxidized α-1,4-oligoglucuronic acid tri-saccharide.
Figure 9:
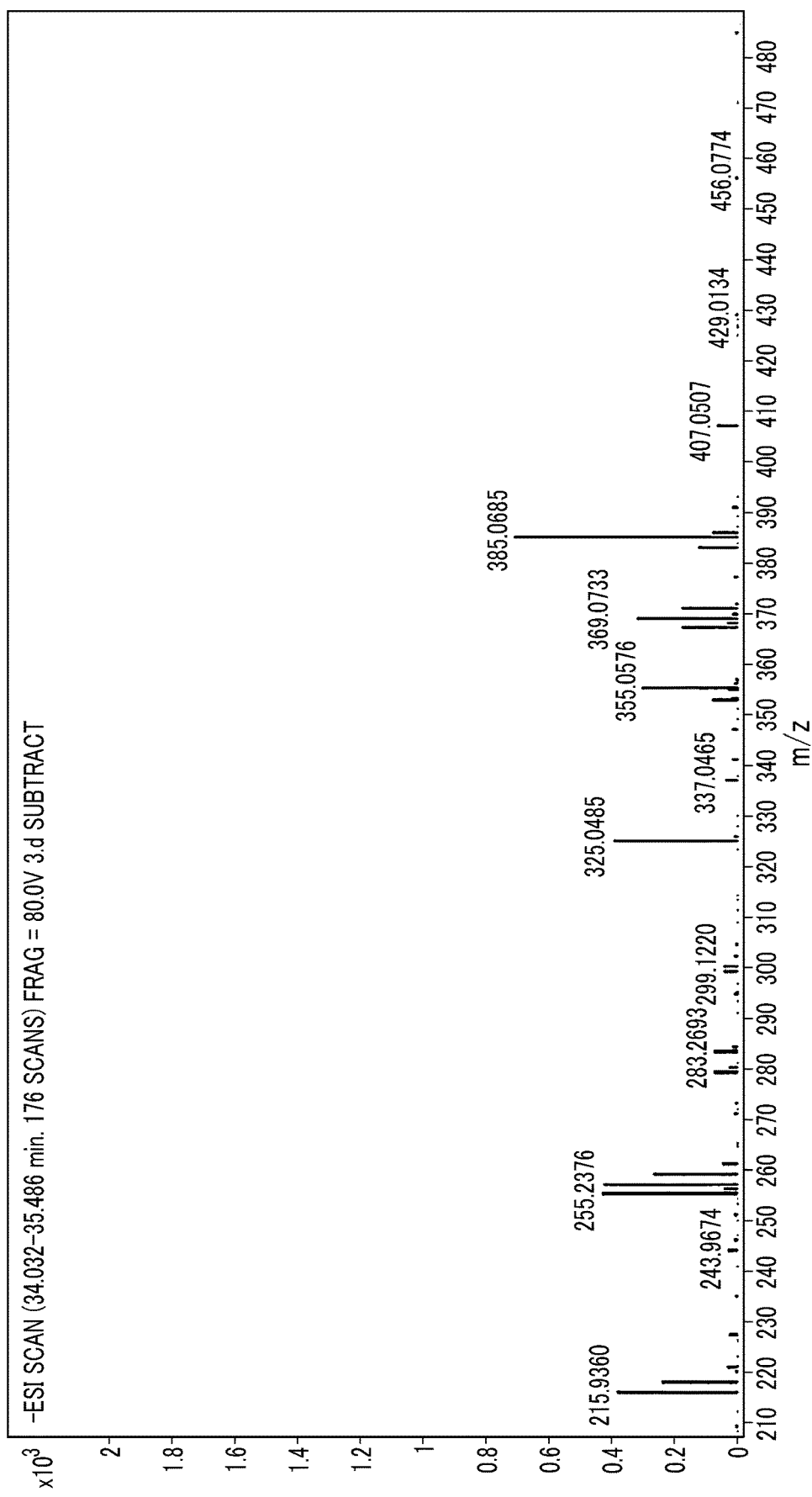
FIG. 9 is a mass spectrum of peak 8 in Example 5, i.e., a mass spectrum of oxidized α-1,4-oligoglucuronic acid bi-saccharide.
Figure 10:
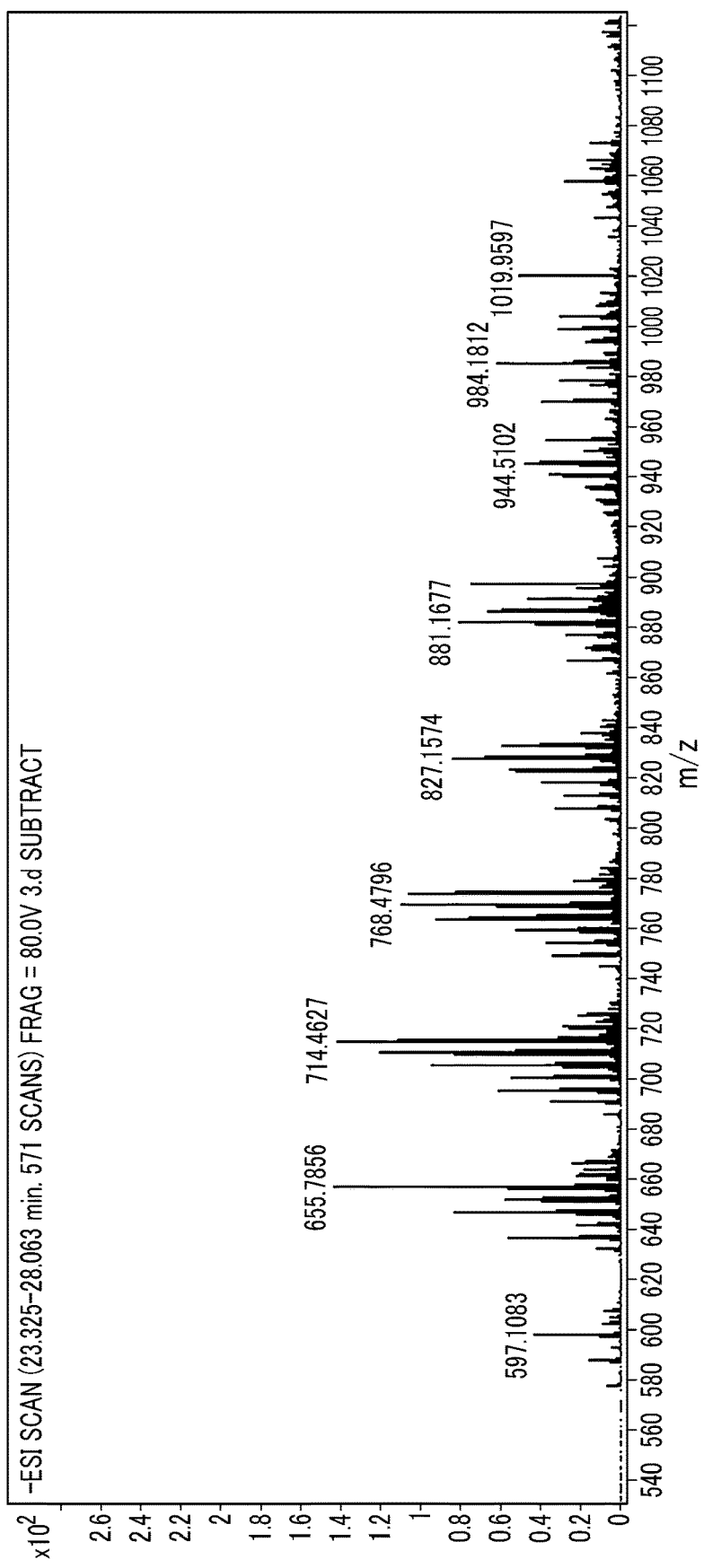
FIG. 10 is a mass spectrum of deca-saccharide to vige-saccharide in Example 5, i.e., a mass spectrum of oxidized α-1,4-oligoglucuronic acid (dp10-dp20)

Upon UHPLC/Q-TOF-MS analysis of oxidized α-1,4-oligoglucuronic acid, following total ion chromatography (TIC) and UV chromatogram were obtained (see FIG. 1). As can be seen from FIG. 1, the peaks are distributed in a regular wave. Since molecular exclusion chromatography column was used, it is speculated that the wave peaks should be distributed from large to small according to polymerization degree. Structures were further speculated according to mass spectrum corresponding to each chromatographic peak (FIG. 2-9): FIG. 2 shows mass spectrum of peak 1, wherein there are two charges for m/z 808.1483, 793.1434 and 778.1382, and upon calculation, the molecular weights of the compounds represented by the three signals are 1618, 1588 and 1558 Da, respectively, and the corresponding structure are oxidized α-1,4-oligoglucuronic acid nonus-saccharide, as shown in Formula I (n=8, m=0, 1 or 2). In addition, there are a few mass spectra signals with two charges, m/z 896.1640, 881.1638 and 866.1564, which are calculated to be three compounds with a molecular weight of 1794, 1764 and 1734 Da, respectively, corresponding to the structure of oxidized α-1,4-oligoglucuronic acid deca-saccharide, as shown in formula I (n=9, m=0, 1 or 2). Similarly, FIGS. 3 to 9 are mass spectra for peaks 2 to 8, which, upon structure analysis, are oxidized α-1,4-oligoglucuronic acid oct-saccharide to bi-saccharide, as shown in formula I (n=7→1, m=0, 1 or 2). In chromatograms, deca-saccharide to vige-saccharide are not well resolved, but there are relative clear signals in mass spectra, as shown in FIG. 10.

Example 6. Nuclear Magnetic Structure Confirmation of Oxidized α-1,4-Oligoglucuronic Acid 6.1 Methods 25 mg of sample of Example 1 was accurately weighed, dissolved in 0.5 ml of heavy water (D≥99.96%) and analyzed by 600 MHz nuclear magnetic resonance spectrometer (Agilent, United States), wherein the concentration of internal standard trimethylsilylpropionate (TSP) was 0.2 μg/ml. Scanning time of hydrogen spectrum is 1 hour, and the test temperature is room temperature. Scanning time of carbon spectrum is more than 12 hour, and the test temperature is room temperature.

6.2 Results

Figure 11:
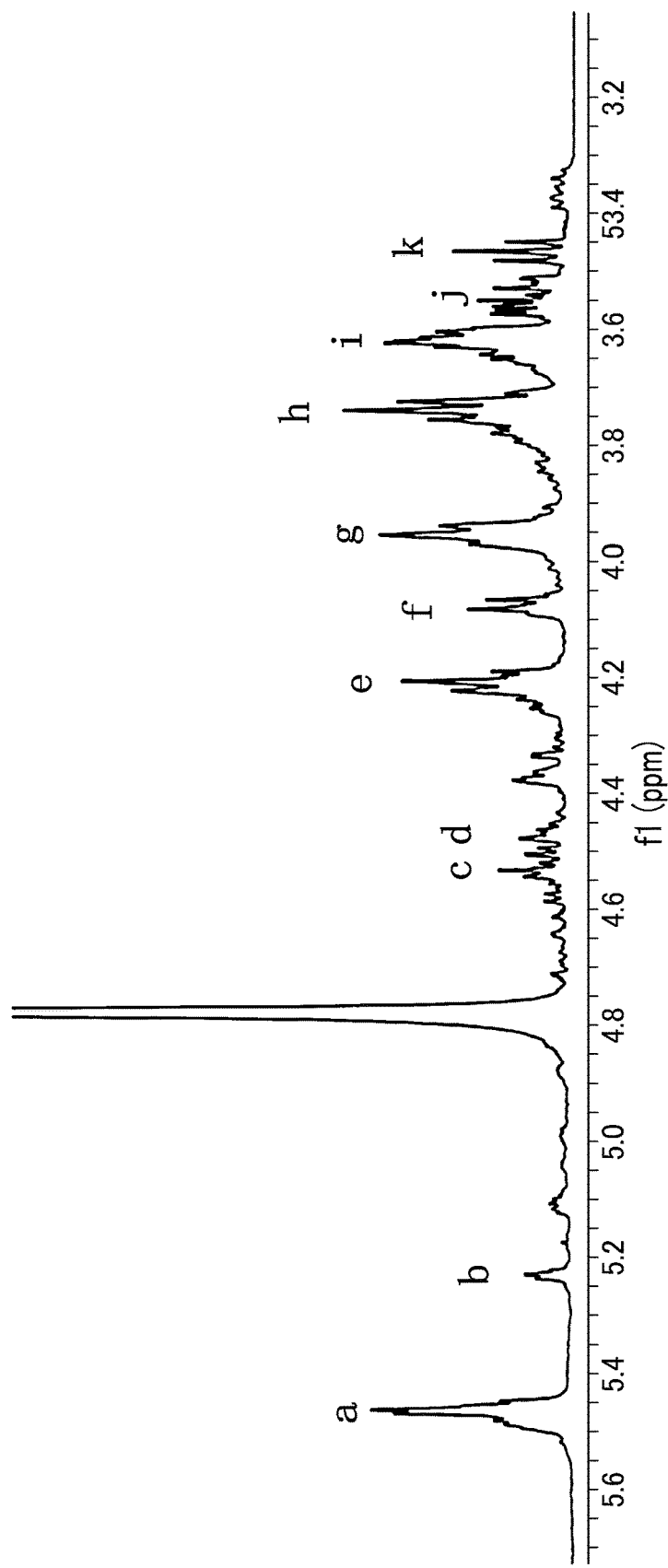
FIG. 11 is a $^1$H-NMR spectrum of the oxidized α-1,4-oligoglucuronic acid in Example 6.
Figure 12:
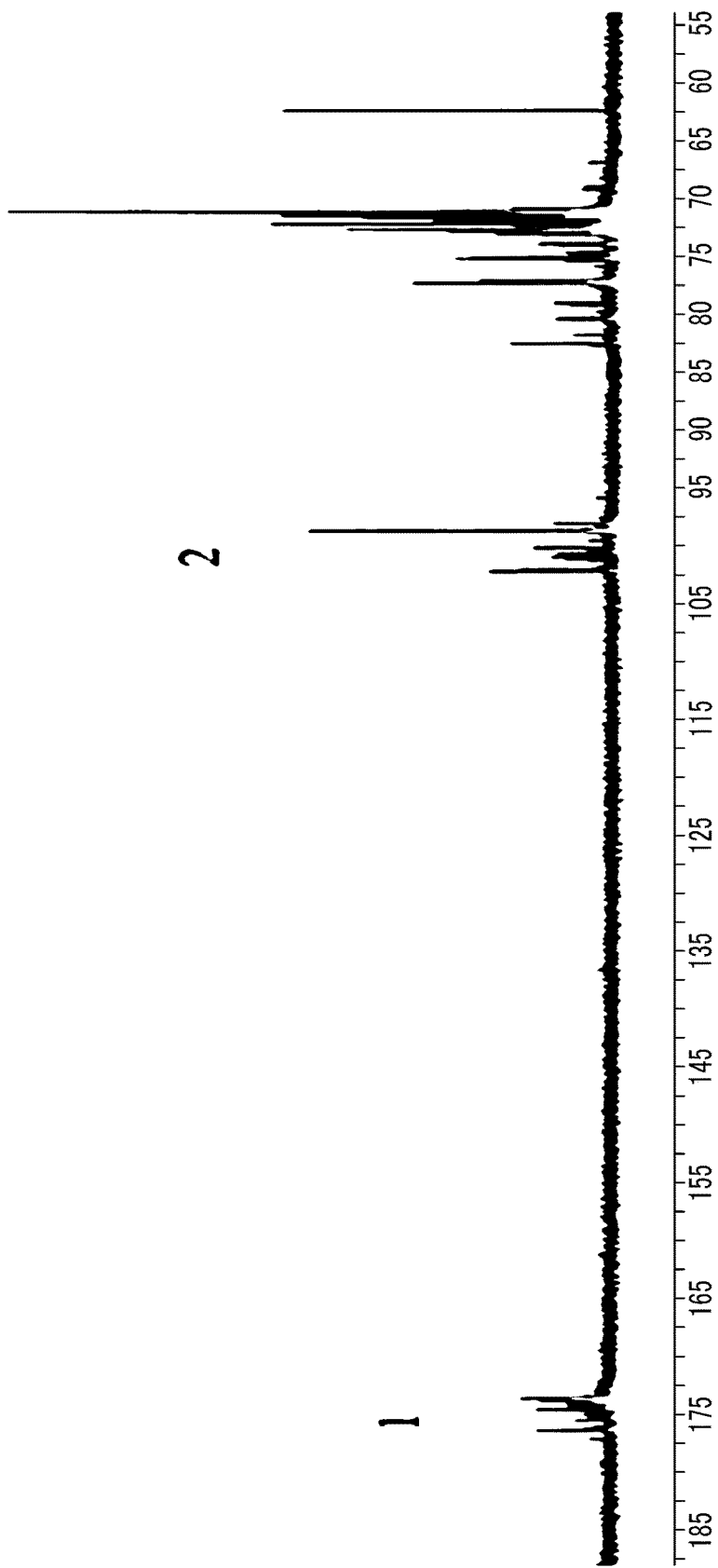
FIG. 12 is a $^{13}$C-NMR spectrum of the oxidized α-1,4-oligoglucuronic acid in Example 6.

NMR results are shown in FIG. 11 ($^1$H-NMR) and FIG. 12 ($^{13}$C-NMR). It can be seen from hydrogen spectrum that a (5.45~5.49 ppm) represents H at the first position of cyclic glucuronic acid of α-configuration which is directly connected to or adjacent to ring-opened uronic acid, and b (5.23 ppm) represents H at the first position of cyclic glucuronic acid of α-configuration which is far apart from ring-opened uronic acid. h (3.74 ppm) represents H at β-position of carboxyl when the reducing terminus of glucuronic acid is ring-opened and (—CH$_2$O—) is not removed, and j (3.55 ppm) represents H at γ-position of carboxyl when the reducing terminus is ring-opened and —CH$_2$O— is not removed or the reducing terminus is ring-opened and —CH$_2$O— is removed. In addition, in the structure of glucuronic acid with ring-opened reducing terminus and without removal of —CH$_2$O—, or with removal of one —CH$_2$O— or two —CH$_2$O—, H connected to hydroxyl and carboxyl can not be found in hydrogen spectrum since the chemical shift of H is close to the chemical shift of water peak. Other peaks are H on the ring of uronic acid without opened-ring. It can be further seen from carbon spectrum that region 1 is peak of carboxy carbon, and region 2 is C at position 1 of uronic acid with closed-ring under different chemical environments. Combining hydrogen and carbon spectra analysis, it can be concluded that position 6 in structure unit of α-glucose was successfully oxidized to carboxyl, and the reducing terminus of glucuronic acid oligosaccharide was ring-opened with a certain degree of degradation, further demonstrating the results of mass spectrometry analysis.

Example 7. Effects of Oxidized α-1,4-Oligoglucuronic Acid on HT-22 Cells Under Oxygen and Glucose Deprivation (OGD) Conditions 7.1 Establishment and Experimental Grouping of OGD Model Normally cultured HT-22 cells were taken, and the number of cells was adjusted to 2×10$^4$ cells/ml. The cells were seeded in 96-well culture plates at 100 µl/well, and quadruplicate was set for each group (n=4). After pre-incubation for 12 hours, in administration group, 10 µl of oxidized products of Example 1 of different concentrations (1, 10, 100 µM) prepared in media were added respectively, and in the normal group, the same volume of media were added. The culture plates were incubated in 5% CO$_2$, 37° C. incubator for 12 h. Cell viability was observed and determined to determine the effects of the samples on normal cultured HT-22 cells.

The normal cultured HT-22 cells were taken, and the original culture medium was removed. The cells were washed twice with sugar-free DMEM medium and sugar-free DMEM medium was added to adjust the number of cells to 2×10$^4$/ml. Cells were inoculated in 96-well culture plates at 100 µl/well. In administration group, 10 µl of oxidized products of Example 1 of different concentrations (1, 10, 100 µM) prepared in media were added respectively, and in the model group, the same volume of media were added. The culture plates were placed in an oxygen deprivation tank (inflated with 95% N$_2$, 5% CO$_2$) and incubated at 37° C. for 12 h. Cell viability was observed and determined to determine the effects of the samples on HT-22 cells under OGD.

7.2 Cell Viability Determined by MTT Assay

After the above groups of cells were cultured, 10 µL of MTT (5 mg/ml) solution was added to each well and cultured for another 4 hours. 100 µl of 10% SDS was added. After purple crystal was completely dissolved, OD values were measured at 570 nm and cell viability was calculated.

7.3 Results

Figure 13:
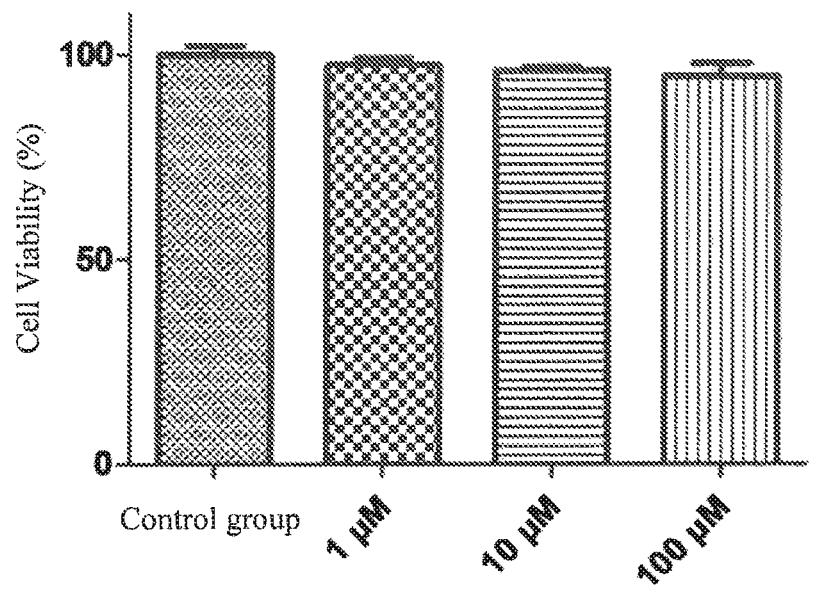
FIG. 13 shows effects of oxidized α-1,4-oligoglucuronic acid in Example 7 on hippocampal cells of normal mice.
Figure 14:
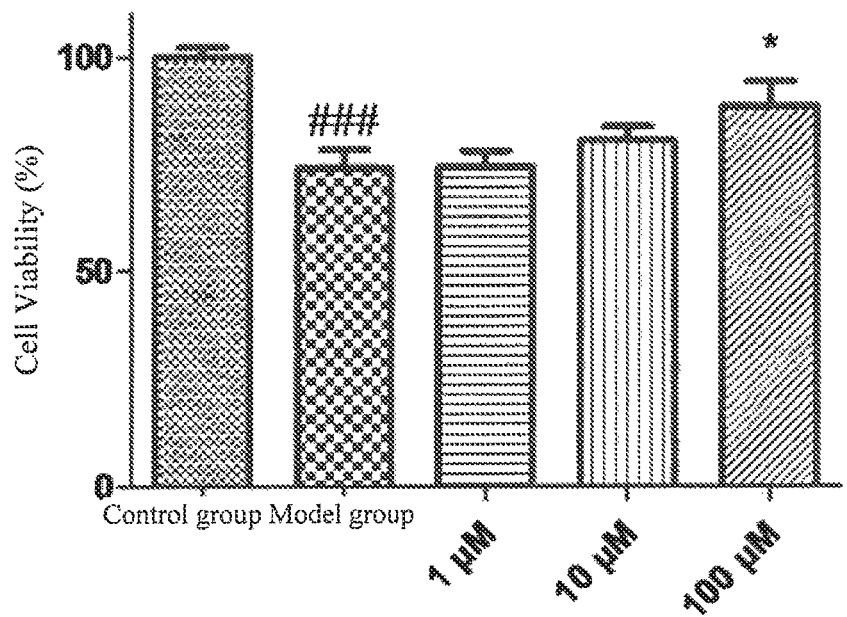
FIG. 14 shows effect of oxidized α-1,4-oligoglucuronic acid in Example 7 on hippocampal cells of glucose and oxygen deprivation mice.

Cell viability in each group was calculated by MTT method, as shown in Table 1, 2 and FIGS. 13, 14. As can be seen from Table 1 and FIG. 13, compared with normal group, there was no significant difference in cell viability after addition of low, medium and high doses of oxidized α-1,4-oligoglucuronic acid, indicating that oxidized α-1,4-oligoglucuronic acid is not toxic to HT-22 cells.

As can be seen from Table 2, compared with the control group, viability of HT-22 cells in the model group was significantly reduced (p<0.001), indicating that OGD significantly inhibited cell viability. However, cell viability increased with addition of oxidized α-1,4-glucuronidic acid (10 µM); when the drug concentration reached 100 µM, cell viability was significantly higher than that of the model group (p<0.05), indicating that oxidized α-1,4-oligoglucuronic acid possesses the effects of promoting the growth of HT-22 cells.

TABLE 1

Effects of oxidized α-1,4-oligoglucuronic acid on viability of normal HT-22 cells

| Groups | Concentration (µM) | Viability (%) |
|---|---|---|
| Control group | | 100.00 ± 2.20 |
| oxidized α-1,4-oligoglucuronic acid | 1 | 97.39 ± 1.77 |
| | 10 | 96.07 ± 0.96 |
| | 100 | 94.78 ± 3.12 |

Data is expressed as mean±SEM
Compared with the control group: p<0.05 significant difference (LSD test)

TABLE 2

Oxidized α-1,4-oligoglucuronic acid on viability of HT-22 cells under OGD

| Groups | Concentration (µM) | Viability (%) |
|---|---|---|
| Control group | | 100.00 ± 2.09 |
| Model group | | 74.03 ± 4.24[###] |
| oxidized α-1,4-oligoglucuronic acid | 1 | 74.18 ± 3.71 |
| | 10 | 80.14 ± 3.32 |
| | 100 | 88.16 ± 5.77* |

Data is expressed as mean ± SEM
[###]indicates p < 0.001 compared with the control group (LSD test)
*Indicates p < 0.05 compared with the model group (LSD test)

It can be seen from the above that oxidized α-1,4-oligoglucuronic acid or a mixture thereof of the present invention possesses a good anti-cerebral ischemia effect and similar results are also obtained in similar experiments using each isolated oxidized α-1,4-oligoglucuronic acid, which are useful in the preparation of anti-cerebral ischemia drugs.

There are various embodiments of the present invention, and all technical solutions formed by similar transformation or equivalent transformation shall fall within the protection scope of the present invention.

The invention claimed is:

1. An oxidized α-1,4-oligoglucuronic acid, consisting of general formula I:

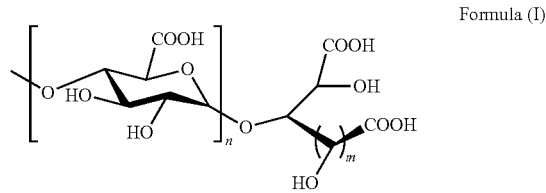

Formula (I)

wherein n is selected from 4-19; and m is selected from 0 or 1.

2. The oxidized α-1,4-oligoglucuronic acid of claim 1, wherein m=0.

3. The oxidized α-1,4-oligoglucuronic acid of claim 1, wherein m=1.

4. The oxidized α-1,4-oligoglucuronic acid of claim 1, wherein n=4–9.

5. The oxidized α-1,4-oligoglucuronic acid of claim 1, wherein n is 4, 5, 6, 7, 8, or 9.

6. A mixture of oxidized α-1,4-oligoglucuronic acids consisting of the structure of general formula I':

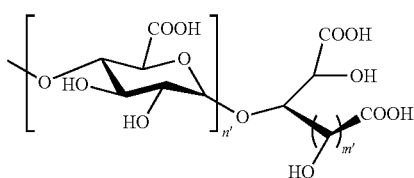

Formula (I')

wherein n' is the average value of n of general formula I of claim 1 and is selected from 4.0 to 19.0; and m' is the average value of m of general formula I of claim 1 and is selected from 0 to 1.0.

7. The mixture of claim 6, wherein the average value of n of formula I is selected from 4.0 to 10.0 and the average value of m of formula I is selected from 0.5 to 1.0.

8. The mixture of claim 6, wherein the components with n of 4-9 account for more than 80% by weight of the mixture.

9. A preparation process for oxidized α-1,4-oligoglucuronic acid of claim 1, comprising following steps:
  (1) weighing and preparing soluble starch into aqueous solution;
  (2) sequentially adding 2,2,6,6-tetramethylpiperidine oxide and sodium bromide to the aqueous solution prepared in step (1), adjusting pH to 10-11 with an alkaline pH adjuster, then adding a sodium hypochlorite solution and reacting for 5-10 hours at 40-70° C., and finally adding an organic solvent to quench the reaction;
  (3) obtaining the oxidized α-1,4-oligoglucuronic acids through dialysis in a 500 Da dialysis bag, concentration and lyophilization.

10. The preparation process of claim 9, wherein mass: volume ratio of the soluble starch to water in step (1) is 1 g:(50~100) ml.

11. The preparation process of claim 9, wherein mass ratio of the soluble starch to 2,2,6,6-tetramethylpiperidine oxide in step (2) is 1000:(5~50).

12. The preparation process of claim 9, wherein mass ratio of NaBr to 2,2,6,6-tetramethylpiperidine oxide in step (2) is ≥10:1.

13. The preparation process of claim 9, wherein mass: volume ratio of the soluble starch to the sodium hypochlorite solution in step (2) is 1 g:(5~15) ml.

14. The preparation process of claim 9, wherein the organic solvent in step (2) is absolute ethanol or methanol.

15. The preparation process of claim 9, wherein the alkaline pH adjuster in step (2) is 5~50% w/v NaOH solution.

16. A pharmaceutical composition, comprising the oxidized α-1,4-oligoglucuronic acid of claim 1 or a mixture of oxidized α-1,4-oligoglucuronic acids consisting of the structure of general formula I':

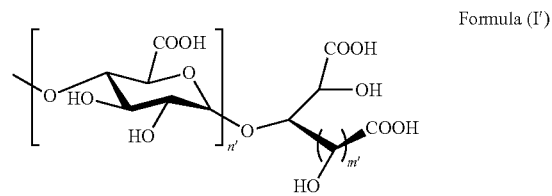

Formula (I')

wherein n' is the average value of n of general formula I of claim 1 and is selected from 4.0 to 19.0; and m' is the average value of m of general formula I of claim 1 and is selected from 0 to 1.0, and a pharmaceutically acceptable excipient or carrier.

17. A method for treating ischemic damage to neurons caused by stroke, myocardial infarction, brain shock, neonatal asphyxia or traumatic brain injury, comprising administering to a subject in need thereof effective amount of the oxidized α-1,4-oligoglucuronic acid of claim 1 or a mixture of oxidized α-1,4-oligoglucuronic acids consisting of the structure of general formula I':

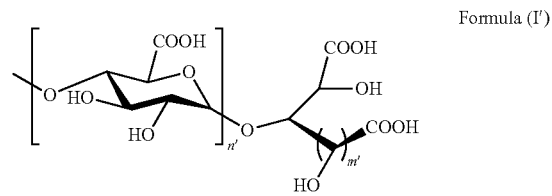

Formula (I')

wherein n' is the average value of n of general formula I of claim 1 and is selected from 4.0 to 19.0; and m' is the average value of m of general formula I of claim 1 and is selected from 0 to 1.0.

18. A mixture of oxidized α-1,4-oligoglucuronic acids consisting of the structure of general formula I':

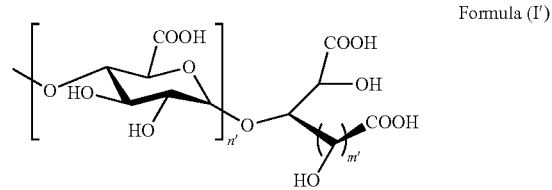

Formula (I')

wherein n' and m' are each a range of average values of n and m, respectively, of all the oxidized α-1,4-oligoglucuronic acids of claim 1.

* * * * *